(12) United States Patent
Schulte (10) Patent No.: US 8,100,983 B2
(45) Date of Patent: Jan. 24, 2012

(54) INTRA-OSSEUS FUSION SYSTEM

(76) Inventor: Robert C. Schulte, Fort Collins, CO (US)

( * ) Notice: Subject to any disclaimer, the term of this patent is extended or adjusted under 35 U.S.C. 154(b) by 139 days.

(21) Appl. No.: 12/592,226

(22) Filed: Nov. 20, 2009

(65) Prior Publication Data

US 2010/0131072 A1  May 27, 2010

Related U.S. Application Data

(60) Provisional application No. 61/200,406, filed on Nov. 25, 2008.

(51) Int. Cl.
*A61F 2/42* (2006.01)
(52) U.S. Cl. ............... 623/21.11; 623/21.15; 623/21.19; 623/23.6
(58) Field of Classification Search ............... 623/21.15, 623/21.19
See application file for complete search history.

(56) References Cited

U.S. PATENT DOCUMENTS

| | | |
|---|---|---|
| 4,969,909 A | 11/1990 | Barouk |
| 5,207,712 A | 5/1993 | Cohen |
| 5,326,366 A | 7/1994 | Pascarella et al. |
| 5,458,648 A | 10/1995 | Berman et al. |
| 5,480,447 A | 1/1996 | Skiba |
| 5,667,510 A | 9/1997 | Combs |
| 5,725,585 A | 3/1998 | Zobel |
| 6,102,954 A * | 8/2000 | Albrektsson et al. ...... 623/20.32 |
| 6,319,284 B1 | 11/2001 | Rushdy et al. |
| 6,454,808 B1 | 9/2002 | Masada |
| 6,699,292 B2 | 3/2004 | Ogilvie et al. |
| 7,037,342 B2 | 5/2006 | Nilsson et al. |
| 7,041,106 B1 * | 5/2006 | Carver et al. ................. 606/309 |
| 7,112,221 B2 | 9/2006 | Harris |
| 7,182,787 B2 | 2/2007 | Hassler et al. |
| 7,291,175 B1 | 11/2007 | Gordon |
| 7,534,244 B2 * | 5/2009 | Ferrante et al. ................. 606/64 |
| 2002/0072803 A1 | 6/2002 | Saunders et al. |
| 2002/0082705 A1 | 6/2002 | Bouman et al. |
| 2004/0053196 A1 | 3/2004 | Mayer et al. |
| 2007/0213831 A1 | 9/2007 | de Cubber |
| 2008/0221697 A1 | 9/2008 | Graser |

* cited by examiner

*Primary Examiner* — David Isabella
*Assistant Examiner* — Brian Dukert
(74) *Attorney, Agent, or Firm* — Craig R. Miles; CR Miles, P.C.

(57) ABSTRACT

Generally, an intra-osseous fusion system which provides an implantable intra-osseous member and a method of implanting the intra-osseous member for bone on growth which retains an amount of digit curvature.

5 Claims, 8 Drawing Sheets

INTRA-OSSEUS FUSION SYSTEM

This U.S. Non-Provisional Patent Application claims the benefit of U.S. Provisional Patent Application No. 61/200,406, filed Nov. 25, 2008, hereby incorporated by reference herein.

I. BACKGROUND

Generally, an intra-osseous fusion system which provides an implantable intra-osseous member and a method of implanting the intra-osseous member for osseointegration which retains an amount of digit curvature.

A significant problem with conventional implants to correct conditions of the interphalangeal joints may be that the configuration of the implant does not sufficiently resist rotation of the phalanx about the longitudinal axis of the implant.

Another significant problem with conventional implants to correct conditions of the interphalangeal joints may be that the configuration of the implant does not generate sufficient interphalangeal joint angle or digit angle of the surgically treated digit. This may be particularly pronounced in surgical correction of the interphalangeal joints of the thumb with linear implants which may impair the ability of the external surface of the surgically correct thumb to contact the externally surface of the second finger in a substantially normal manner.

Another significant problem with conventional implants to correct conditions of the interphalangeal joints may be that the implant may generate a lesser or greater than desired level of osseointegration with the bone. A lesser than desired amount of osseointegration may lead to detachment of the bone from the implant while a greater than desired amount osseointegration may substantially increase the difficulty associated with adjustment of the location of the implant relative to the treated interphalangeal joint or replacement of the implant.

The invention described herein addresses the problems associated with conventional implants used in surgical correction of the interphalangeal joints of the digits.

II. SUMMARY OF THE INVENTION

Accordingly, a broad object of the invention can be to provide an intra-osseous fusion system which provides an implantable intra-osseous member configured to reduce the rotation of the treated phalanx about the longitudinal axis of the implant.

Another broad object of the invention can be to provide an intra-osseous fusion system which provides an implantable intra-osseous member which can be generated in a linear condition or in an arcuate condition to impart a lesser or greater level of interphalangeal joint angle to the treated interphalangeal joint to achieve a desired level of digit curvature.

Another broad object of the invention can be to provide an intra-osseous fusion system which provides a coat applied or generated over a part or parts of the implantable intra-osseous member to generate the desired level of osseointegration with the bone of the treated phalanx.

Naturally, further objects of the invention are disclosed throughout other areas of the specification, drawings, photographs, and claims.

IV. DETAILED DESCRIPTION OF THE PREFERRED EMBODIMENTS

Generally, an intra-osseous fusion system which provides an implantable intra-osseous member and a method of implanting the intra-osseous member for bone on growth which retains an amount of digit curvature.

Figure 1:
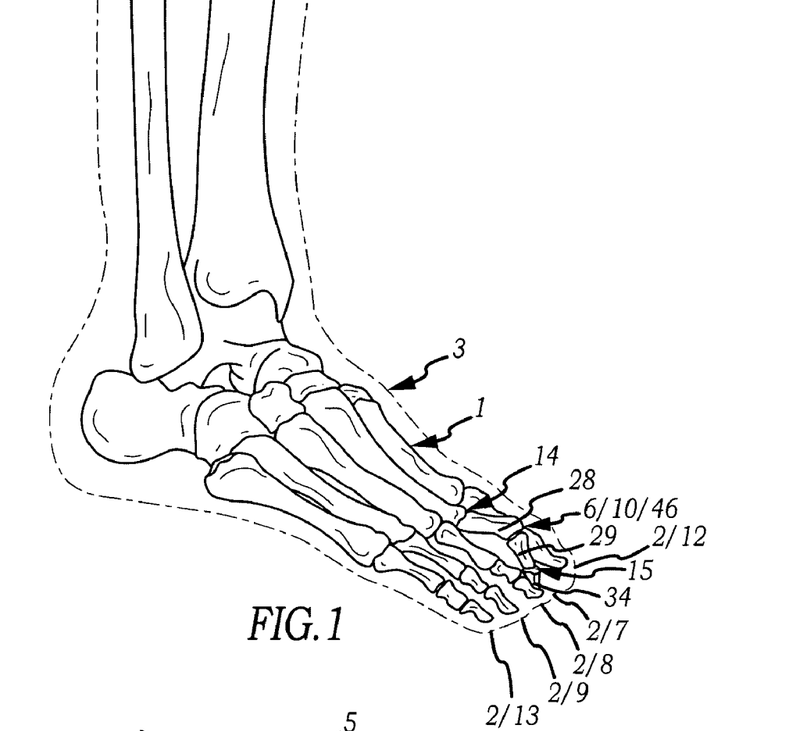
FIG. 1 is an illustration of the bones of a foot which provides a particular example of curvature of a toe which can be treated using particular embodiments of the inventive intra-osseous member.
Figure 2:
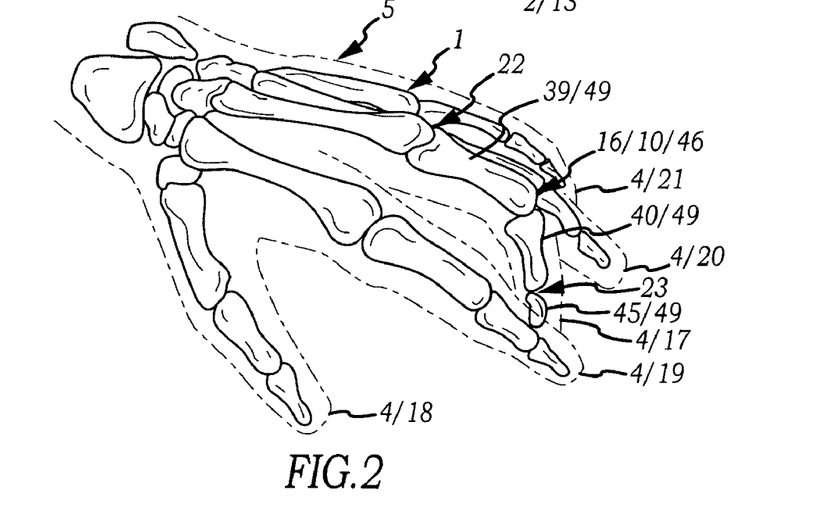
FIG. 2 is an illustration of the bones of a hand which provides a particular example of curvature of a finger which can be treated using particular embodiments of the inventive intra-osseous member.

Now referring primarily to FIGS. 1 and 2, each of which provide an illustration of a medical condition in which the bones (1) of one or more toes (2) of the foot (3) or one or more fingers (4) of the hand (5) have an undesired relation which may require surgical correction. As non-limiting examples, the undesired relation or undesired condition may be due to impact injury, shortened musculature, damage to muscles, nerves, or joints from stroke, osteoarthritis, rheumatoid arthritis, stroke, charcot-Marie-Tooth disease, diabetes, or the like.

Now referring primarily to FIG. 1, as a non-limiting example, a medical condition in which one or more toes (2) are permanently fixed in a curved or a bent condition (10) is commonly referred to as "hammertoe" or "clawtoes". Hammertoe typically relates to a deformity of a middle toe joint (6) of a second toe (7), a third toe (8), or a fourth toe (9) of a foot (3) causing any one or all of the toes (7)(8)(9)(12) of the foot (3) to be permanently bent. Once permanently bent or fixed in a bent condition (10), the toes (7)(8)(9)(12) may require surgical correction. While FIG. 1 shows a hammertoe as a permanent deformity of the middle toe joint (6) of the second toe (7), this is not intended to be limiting with respect to the use of various embodiments of an implantable intra-osseous member (11) (further described below) to correct the hammertoe deformity, the clawtoe deformity, or similar toe condition or deformity in the first toe (12), the second toe (7), the third toe (8), the fourth toe (9) or the fifth toe (13), or more than one of the toes (2) or all of the toes (7)(8)(9)(12)(13) at the middle toe joint (6) or at the upper toe joint (14) or the lower toe joint (15) or in two of the toe joints (6)(14)(15) or three of the toe joints (6)(14)(15) (each whether of the foot (3) or the hand (5) also referred to generally as an "interphalangeal joint" (46)) in various permutations and combinations. Additionally, while the term "hammertoe" may used to describe the deformity shown in FIG. 1, it is not intended that the term "hammertoe" limit the use of the intra-osseous member (11) solely to surgical correction of hammertoe. Rather, embodiments of the intra-osseous member (11) can be used in surgical correction of any of a numerous and wide variety of conditions or deformities of any one or more of the toe(s) (2) at any one or more of the interphalangeal joints (46).

Now referring primarily to FIG. 2, which provides an illustration of similar undesired relation of the bones (1) of a middle finger joint (16) (also referred to as the "proximal interphalangeal joint") of a third finger (17) of the hand (5) causing the third finger (17) to be fixed in a bent condition (10). Similar deformity or other condition of the first finger (18) (also referred to as the "thumb"), the second finger (19), the third finger (17), the fourth finger (20) or the fifth finger (21) may also occur. Once permanently fixed in the bent condition (10) or other undesired condition, correction may require surgery. While FIG. 2 only shows a bent condition (10) or deformity of the middle finger joint (16) of the third finger (17), this is not intended to be limiting with respect to the use of the various embodiments of the implantable intra-osseous member (11) in surgical correction of the bent condition (10) or deformity in the thumb (18), the second finger (19), the fourth finger (20), or the fifth finger (21), or more than one of the fingers (4) or all of the fingers (4) at the middle finger joint (16) (also referred to as the "proximal interphalangeal joint") or at the upper finger joint (22) (also referred to as the "first joint") or the lower finger joint (23) (also referred to as the "distal interphalangeal joint") or in two of the joints (16)(22)(23) or three of the joints (16)(22)(23) (referred to generally as an "interphalangeal joint" (46)) in various permutations and combinations. Fingers (4) and toes (2) may also be generally referred to as "digits".

Now referring to primarily to FIGS. 3, 4, 6 and 7 which show non-limiting examples of the implantable intra-osseous member (11) used to fix the relation between the articulating surfaces (24)(25) (see specifically the example of FIG. 4), or resection surfaces (26)(27) (see specifically the example of FIG. 4) for the purpose of arthodesis, of the proximal phalanx (28) and the middle phalanx (29) of the second toe (7) to prevent reoccurrence of the bent condition (10) of the second toe (7). Also referring to FIGS. 9 and 10 which show non-limiting examples of the implantable intra-osseous member (11) used to fix the relation between the articulating surfaces (24)(25)(30)(31), or the resection surfaces (26)(27)(32)(33) for the purpose of arthodesis, of the proximal phalanx (28) and the middle phalanx (29) and the distal phalanx (34) of the second toe (7) to prevent reoccurrence of the bent condition (10) of the second toe (7) as shown in FIG. 1.

Figure 5:
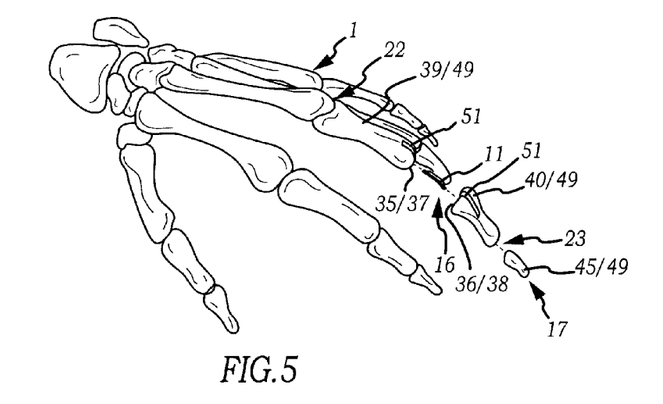
FIG. 5 is an exploded view of the bones of a hand which provides an example of a particular embodiment of the inventive intra-osseous member used to correct curvature of a finger.
Figure 6:
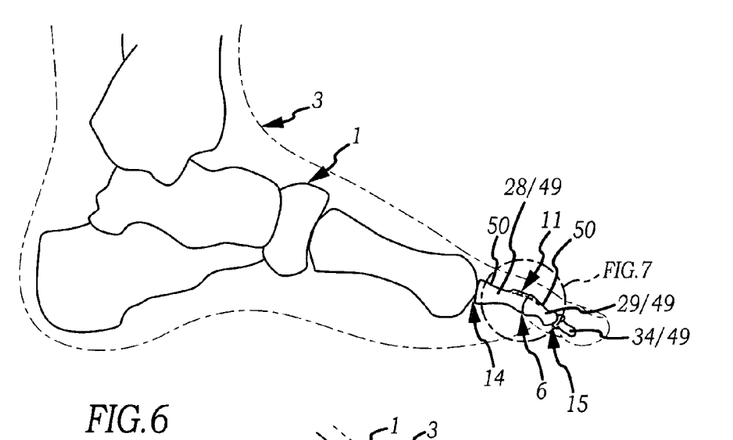
FIG. 6 is a side view of the bones of a foot which provides an example of a particular embodiment of the inventive intra-osseous member used to correct curvature of a toe.
Figure 7:
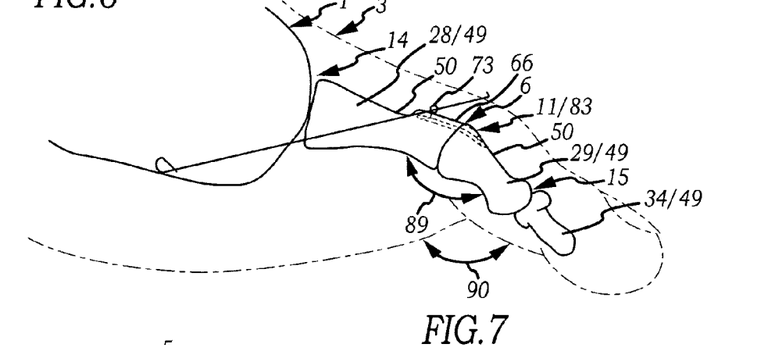
FIG. 7 is an enlargement of a part of the side view of FIG. 6 which provides a particular example of use of a particular embodiment of the inventive intra-osseous member with an annular member and wire retainer used to correct curvature of a toe.
Figure 8:
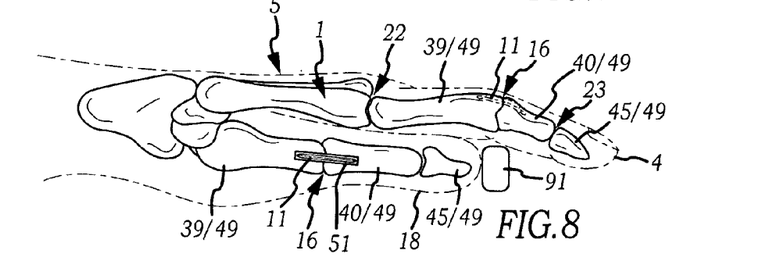
FIG. 8 is a side view of the bones of a hand which provides an example of a particular embodiment of the inventive intra-osseous member used to correct curvature of a finger.

Similarly, referring primarily to FIGS. 5 and 8, which show non-limiting examples of the implantable intra-osseous member (11) used to fix the relation between the articulating surfaces (35)(36), or resection surfaces (37)(38) for the purpose of arthodesis, of the proximal phalanx (39) and the intermediate phalanx (40) of the third finger (17) to prevent reoccurrence of the bent condition (10) of the third finger (17). Also, referring to FIG. 11, which provides a non-limiting example of the implantable intra-osseous member (11) used to fix the relation between the articulating surfaces (35)(36)(41)(42), or the resection surfaces (37)(38)(43)(44) for the purpose of arthodesis, of the proximal phalanx (39), the middle phalanx (40) and the distal phalanx (45) of the third finger (17) to prevent reoccurrence of the permanent bent condition (10) shown in FIG. 2.

Surgical correction of the deformities utilizing various embodiments of the intra-osseous member (11), further described below, can for example be achieved by anesthesia of the digit of the hand or foot (for example, 3 to 4 cc 0.5% bupivicaine in conventional v-block fashion) followed by exposure of the interphalangeal joint (46) (referring to any of the upper (14), middle (6), or lower (15) joints of the toes (2) or the upper (22), middle (16), or lower (23) joints of the fingers (4), as above described each an interphalnageal joint (46) although for clarity only the example in FIG. 2 includes a numerical identifier), by incision. Depending on the interphalangeal joint (46) to be exposed the use of dorsal linear, dorsal longitudinal semi-elliptical, dorsal transverse semi-elliptical, plantar longitudinal and medial/lateral incisions can be made with a blade, such as a number 15 blade. Medial incisions to the second digits and fifth digits and lateral incisions to the third and fourth digits may be sufficient to expose the interphalangeal joint (46). However, this description is not intended as a substitute for currently accepted surgical procedures to expose the interphalangeal joint (46) to be surgically corrected.

Upon exposure of the interphalangeal joint (46), the neurovascular structures can be identified and retracted as necessary. The incision can be deepened with sharp dissection of the capsule of the interphalangeal joint (46). The extensor mechanism can then be identified and the blade passed between the extensor tendons and bone (1), separating the bone (1) from the extensor hood. Then the medial and lateral collateral ligaments can be released allowing access to the corresponding phalangeal heads (47) (see FIG. 4 for example) of the exposed interphalangeal joint (46). As to certain procedures, a bone cutter can be used to transect a part or all of the phalangeal heads (47) and part or all of the phalangeal heads (47) can be removed. A bone rasp can be used to smooth and remove any bone spicules.

Figures 3, 4:
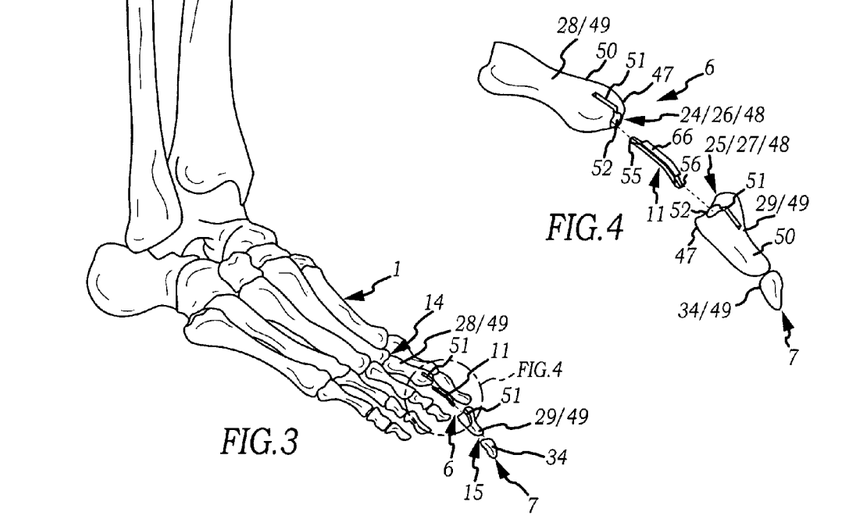
FIG. 3 is an exploded view of the bones of a foot which provides an example of a particular embodiment of the inventive intra-osseous member used to correct curvature of a toe.
FIG. 4 is an enlargement of a part of the exploded view of FIG. 3 which provides a particular example of use of a particular embodiment of the inventive intra-osseous member used to correct curvature of a toe.

Now referring primarily to FIG. 4, the resected parts of the interphalangeal heads (47) of the interphalangeal joint (46) can provide a corresponding pair of resection surfaces (48) (referring to any of the pairs of resection surfaces (26)(27), (32)(33), (37)(38), (43)(44) of the interphalangeal joints (46) of the hand (5) or the foot (3), above described) each substantially perpendicular to the corresponding central canal of each phalanx (49) (referring to any of the phalanx (28)(29)(34)(39) (40)(45) of the hand (5) or the foot (3) as above described). A saw or other bone cutting tool can be used to generate a channel (51) on the dorsal surface (50) of each phalanx (49) substantially aligned with the longitudinal midline and terminating at each of the pair of resection surfaces (48) having predetermined depth. The length and depth of each channel (51) depends upon the particular one of the phalanx (49) involved in the surgical correction of the deformity or condition.

Figure 20:
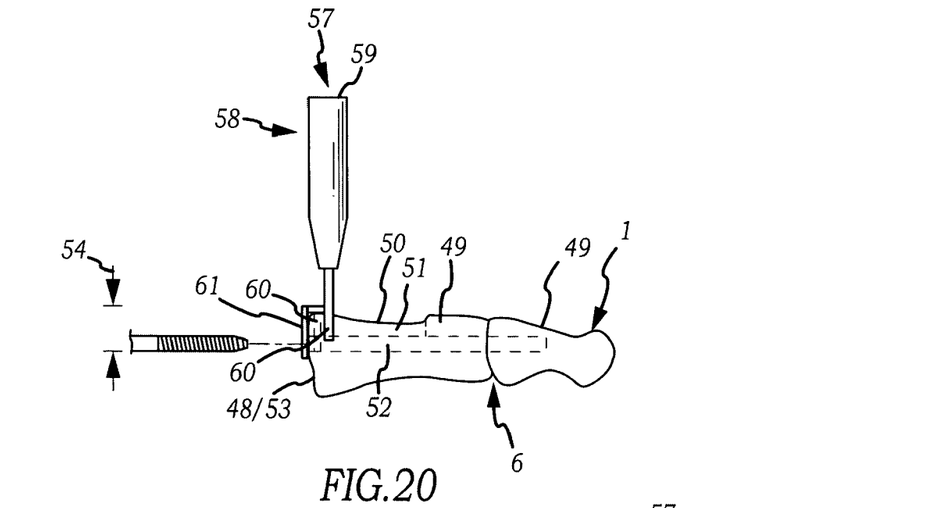
FIG. 20 is a side view of a particular embodiment of a borehole location tool used to locate a borehole in the articulation or resection surface of a phalanx.

Now referring specifically to FIG. 20, a borehole (52) can be established in the phalanx (49) commencing at an articulating surface (53) (referring to any of the articulating surfaces (24)(25)(30)(31) of the bones (1) of the foot (3) or the articulating surfaces (35)(36)(41)(42) of the hand (5) above described) exposed or resection surface (48) generated by the surgical procedure above-described. The borehole (52) projects a distance inward longitudinally at a depth (54) below the dorsal surface (50) of the phalanx (49) to allow the channel (51) to adjoin the periphery of the borehole (52) producing a single hollow configured to receive a first member end (55) or a second member end (56) of the intra-osseous member (11) as shown for example by FIG. 4. As to certain embodiments of the procedure, the borehole (52) can be extended longitudinally to communicate with the opposed articulated surface (53) or opposed resection surface (48) of the phalanx (49). A borehole (52) can be established in the adjacent phalanx (49) to receive a first member end (55) or a second member end (56), as shown for example in FIG. 10.

Figure 21:
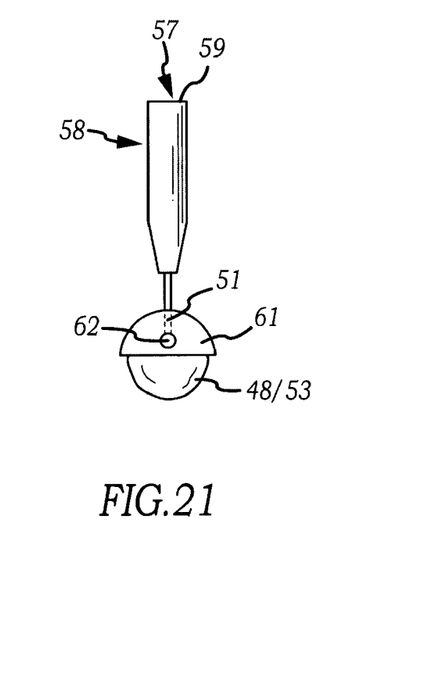
FIG. 21 is front view of a particular embodiment of a borehole location tool used to locate a borehole in the articulation or resection surface of a phalanx.

Again referring primarily to FIGS. 20 and 21, the location of the borehole (52) in relation to the articulated surface (53) or the resection surface (48) to adjoin the channel (51) can be established by use of a borehole location tool (57). The borehole location tool (57) can provide a handle (58) having a length disposed between a grip end (59) and a channel tab (60). A borehole placement template (61) having template aperture (62) can be coupled in fixed relation to the channel tab (60) such that upon insertion of the channel tab (60) into the channel (51) cut into the dorsal surface (50) of the phalanx (49) the template aperture (62) can be drawn adjacent the articulation surface (53) or resection surface (48) of the phalanx (49) to establish the location of the longitudinal axis of the borehole (52).

Figures 14, 15, 16:
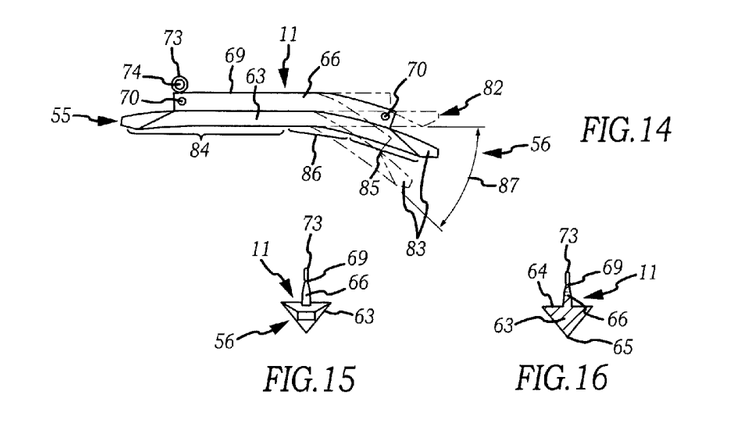
FIG. 14 is a side view of particular embodiments of an intra-osseous member having a bend angle.
FIG. 15 is an end view of a particular embodiment of an intra-osseous member.
FIG. 16 is cross section view 16-16 of a particular embodiment of an intra-osseous member.

Now generally referring to FIGS. 12-16, a particular embodiment of the intra-osseous member (11) can include an elongate member (63) having a substantially triangular configuration in cross section perpendicular to the longitudinal axis as shown in FIG. 16. As a non-limiting example, a particular embodiment of the elongate member (63) can have a length disposed between a first member end (55) and a second member end (56) in the range of about three-quarters of an inch to about one inch. Now referring specifically to FIG. 16, the height of the triangular cross section from the base (64) of the triangle to the apex (65) can be in the range of about one-sixteenth inch to about one-eighth inch. However, the dimensional configuration of a particular inter-osseous member (11) will depend upon the dimensional configuration of the interphalangeal joint(s) (46) being surgically corrected. The elongate member (63) can taper approaching the first member end (55) and the second member end (56). Certain embodiments of the elongate member (63) taper toward the mid-line of the base (64) of the triangular configuration of the elongate member (11) approaching each of the corresponding first member end (55) and second member end (56) and truncate the triangular configuration toward the base (64) approaching each of the corresponding first member end (55) and second member end (56) to generate terminals of the first member end (55) and the second member end (56) which can be substantially rectangular or square in end view as shown in FIG. 15. As one non-limiting example, the rectangular or square terminal of the first member end (55) or the second member end (56), or both, can have a length on each side in the range of about one-thirty second inch to about one-sixteenth inch. While the examples of FIGS. 12-19 show embodiments of the invention with a elongate member (63) with a substantially triangular configuration in cross-section the invention is not so limited and alternate embodiments of the invention can provide circular, square, rectangular, oval, pentagonal, or other cross-sectional configurations which can further include the additional elements herein described.

The intra-osseous member (11) can further include a projection element (66) coupled to the base of the elongate member (63). In the particular embodiment of the intra-osseous member (11) shown in FIGS. 12-16, the projection element (66) couples along the longitudinal midline of the base (64) of the triangular elongate member (63). The projection element (66) can have a length disposed between a pair of projection element ends (67)(68) in the range of about one-half to three-quarters the length of the elongate member (63) and a height in the range of about one-thirty second inch and about one-sixteenth of an inch depending upon the application. As to certain embodiments of the intra-osseous member (11), the height can be matched to the depth of the channel (51) above described so that upon insertion of a first member end (55) or the second member end (56) into the borehole (52) the projection element (66) axially slidly inserts into the channel (51) establishing the projection terminal (69) of the projection element (66) substantially flush with the dorsal surface (50) of the phalanx (49). However, as to other embodiments of the intra-osseous member (11), the projection element (66) can be configured to extend a distance outward from the dorsal surface (50) of the phalanx (4). In certain embodiments, the outward extension of the projection element (66) can be as much as one-sixteenth of an inch.

Figure 12:
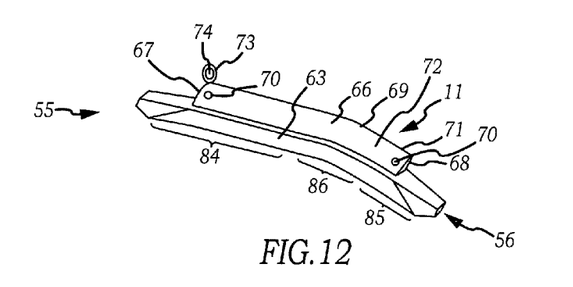
FIG. 12 is a perspective view of a particular embodiment of an intra-osseous member.
Figure 13:
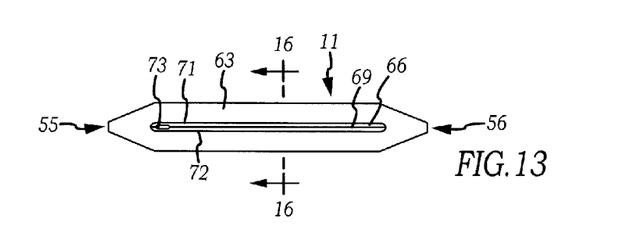
FIG. 13 is a top view of a particular embodiment of an intra-osseous member.

Now referring primarily to FIG. 12, the projection element (66) can further define a lateral bore (70) proximate each of the pair of projection element ends (67)(68) which communicates between a first projection element side (71) and a second projection element side (72). Each lateral bore (70) can be configured to receive a wire having a diameter in the range of about 0.015 inch (about a 28 gauge wire) and about 0.080 inch (about a 14 gauge wire).

Again referring to FIG. 12, the projection element (66) can further include a annular member (73) coupled proximate to one or both of the pair of projection element ends (67)(68). The annular member (73) can define an opening (74) which can receive a wire having a diameter in the range of about 0.015 inch (about a 28 gauge wire) and about 0.080 inch (about a 14 gauge wire).

Figure 22:
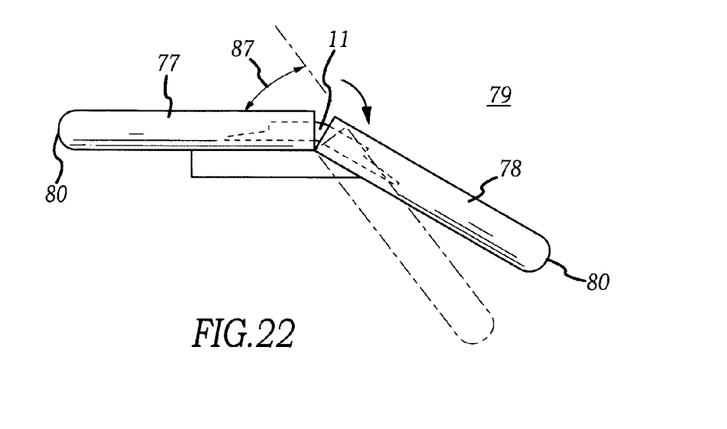
FIG. 22 is side view of a particular embodiment of an intra-osseous member bending tool showing a particular method of generating a particular arcuate embodiment of an intra-osseous member.
Figure 23:
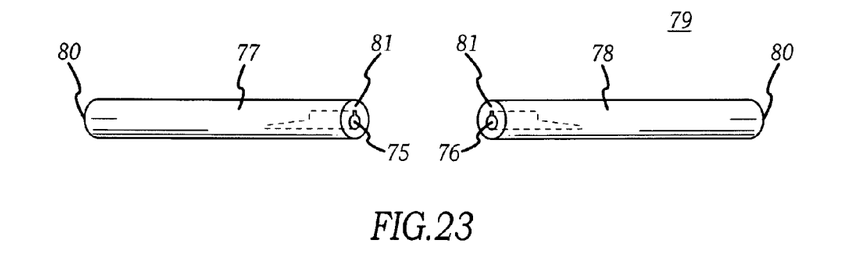
FIG. 23 is a perspective view of a particular embodiment of an intra-osseous member bending tool.

Now referring primarily to FIGS. 14, 22 and 23, the first member end (55) and the second member end (56) of linear embodiments of the intra-osseous member (11) (also referred to as the "linear condition" (82)) (see for example FIG. 14) can correspondingly slidly insert into a pair of hollow spaces (75)(76) of a pair handles (77)(78) of a intra-osseous member bending tool (79). The pair of handles (77)(78) can have a sufficient length disposed between a first handle end (80) and a second handle end (81) which allows a person gripping the external surface of each of the pair of handles (77)(78) in a corresponding hand to generate the curved portion (86) in the linear condition (82) of intra-osseous member (11) substantially perpendicular to the longitudinal axis of the intra-osseous member (11) to provide curved, bent or arcuate embodiments of the intra-osseous member (11) (also referred to as the "arcuate condition") (83). The term "arcuate condition" encompasses embodiments of the intra-osseous member (11) which have greater or lesser curvature along the entire longitudinal axis of the elongate member (63) and embodiments of the intra-osseous member (11) which provide curved portion (86) of greater or lesser curvature intermediate along the longitudinal axis of the elongate member (63) flanked by a first linear segment (84) and a second linear segment (85), as shown for example in FIG. 14. The location of the bend or curvature along the longitudinal axis of the intra-osseous member (11) can vary depending upon the application but can be located about one-half the distance between the middle and the first member end (55) or the second member end (56)(see FIGS. 12 and 14 for example) of the intra-osseous member (11). As to particular embodiments of the intra-osseous member (11), the bend will be toward the apex (65) of the triangular configuration of the elongate member (63) as shown in FIG. 14; however, as to certain embodiments the bend can be toward the base (64) of the triangular configuration of the elongate member (63). While the intra-osseous member bending tool (79) and the method of generating the arcuate condition (83) of the intra-osseous member (11) using the intra-osseous member bending tool (79) provides a means of producing the arcuate condition (83) of the intra-osseous member (11), the invention is not so limited and the arcuate condition (83) can be generated by any of a numerous and varied approaches such as machining, fabrication, casting, molding, hydraulic pressing, or the like.

Now referring primarily to FIG. 14, particular embodiments of the arcuate condition (83) of the intra-osseous member (11) can provide a bend angle (87) in relation to the linear condition (82) in the range of about one degree to about fifty degrees. Certain embodiments of the arcuate condition (83) of the intra-osseous member (11) can provide a bend angle (87) in relation to the linear condition (83) in the range of about thirty degrees to about fifty degrees. However, the bend angle (87) is not so limited and embodiments of the intra-osseous member (11) in the arcuate condition (83) can include any manner of bend angle (87) useful in surgical correction of a finger (4) or toe (2).

Figure 19:
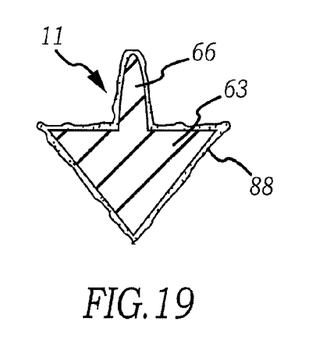
FIG. 19 is a cross section view 19-19 of a particular embodiment of the particular intra-osseous member shown in FIG. 17.

Now referring primarily to FIG. 19, the intra-osseous member (11) can further include a coat (88) coupled to or generated on all or a part of the external surface of the intra-osseous member (11). The coat (88) can be any composition which can be coupled to the intra-osseous member (11) capable of biocompatible osseointegration with the bone of the surgically treated phalangeal joint (46). The intra-osseous member (11) can be produced from a numerous and wide variety of corrosion resistant biocompatible steels and titanium alloys, or the like. The coat (88) can be one or more of pure alumina, titanium-dioxide and hydroxiapatite, or the like. As a non-limiting example, the coat (88) can be applied by plasma spraying with a plasma torch, plasmatron or a plasma gun. Alternately, the coat (88) can be achieved by producing a surface roughness, porosity, or irregularity of the intra-osseous member (11) by sand blasting, bead blasting, molding, or the like. As shown by FIG. 19, the coat (88) can have a thickness in the range of about 40 µm and about 100 µm.

Figure 17:
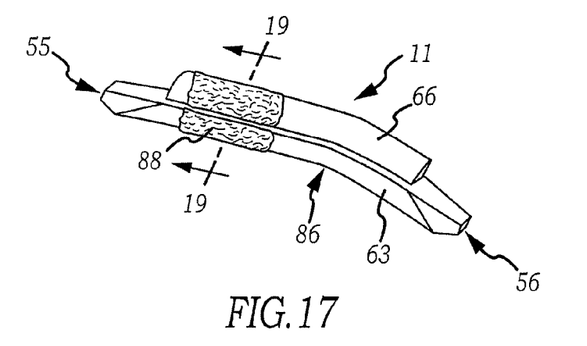
FIG. 17 is perspective view of a particular embodiment of an intra-osseous member having a coat on a part of the external surface.
Figure 18:
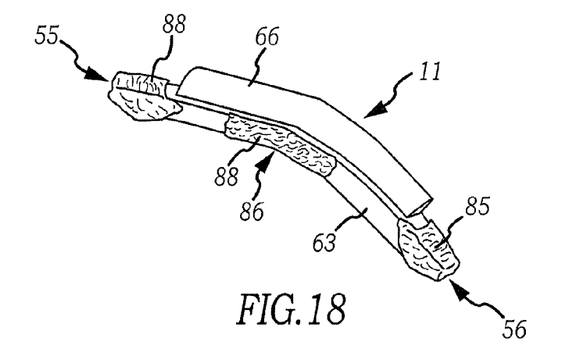
FIG. 18 is perspective view of another particular embodiment of an intra-osseous member having a coat on parts of the external surface.

Now referring specifically to FIGS. 17 and 18, the coat (88) can be applied or generated on a part or a plurality of parts of the intra-osseous member (11). The part or parts of the intra-osseous member (11) to which the coat (88) can be applied or generated may depend upon the level of osseointegration to be achieved between the intra-osseous member (11) and the corresponding part of the bone (1) of the surgically treated phalangeal joint (46).

Because the coat (88) can substantially increase the level of osseointegration between the intra-osseous member (11) and the corresponding part of the bone (1) surgically treated, a coat (88) applied or generated on the entire intra-osseous member (11) can increase the difficulty of any subsequent adjustment, removal or replacement of the intra-osseous member (11). Accordingly, certain embodiments of the intra-osseous member (11) (see for example FIG. 17) can have the coat (88) applied or generated on only a part of the intra-osseous member (11) which correspondingly engages a part of only one phalanx (49) of the interphalangeal joint (46) surgically treated. Alternately, as shown for example in FIG. 18, certain embodiments of the intra-osseous member (11) can have the coat (88) applied or generated proximate the first member end (55) or proximate the second member end (56), or proximate both the first member end (55) and the second member end (56). Also, as shown for example in FIG. 18, the coat (88) can be applied or generated on a part of the intra-osseous member (11) which correspondingly engages both of the phalanx (49) of the interphalangeal joint (46) surgically treated. Understandably, the extent of the coat (88) of the inter-osseous member (11) can be adjusted depending on the level of osseointegration to be achieved and includes the range between the entire surface area of the intra-osseous member (11) to a limited part of the intra-osseous member (11) which correspondingly engages a limited part of one phalanx (49).

Again referring primarily to FIGS. 3-5, the first member end (55) and the second member end (56) of embodiments of the intra-osseous member (11) can be correspondingly inserted into the boreholes (52) generated in a pair of phalanx (49) with the projection element (66) received in the channel (51) cut into each of the pair of phalanx (49). Now referring primarily to FIGS. 6-8, the pair of phalanx (49) can by forcible urging be axially slidly established in the desired fixed relation to each other and in relation to the intra-osseous member (11). As to those embodiments of the intra-osseous member (11) which provide arcuate condition (83) as above-described the articular surfaces (53) or the resection surfaces (48) of the pair of phalanx (49) can be located in fixed relation to first member end (55) and the second member end (56) such that the bend angle (87) locates at the engagement of the articular surfaces (53) or resection surfaces (48) to establish an interphalangeal joint angle (89) generated by the arcuate condition (83) of the intra-osseous member (11). Establishing the interphalangeal joint angle (89) to that generated by arcuate condition (83) of the intra-osseous member (11), can achieve a digit angle (90) of the treated finger (4) or toe (2). The digit angle (90) can be adjusted by use of a lesser or greater bend angle (810) of the intra-osseous member (11).

Now referring specifically to FIG. 8, embodiments of the intra-osseous member (11) can have a configuration which can be located between a pair phalanx (49) of the thumb (18). Use of an intra-osseous member (11) in the linear condition (82) can impair contact of the external surface of the thumb (18) and the external surface of any one or more fingers (4) or grippable contact with objects (91) held between the thumb (18) and the any of the fingers (4). Use of an intra-osseous member (11) in the arcuate condition (83) can generate a corresponding digit angle (90) which can improve contact of the thumb (18) and any one or more of the fingers (4) or grippable contact with objects (91) held between the thumb (18) and any one or more of the fingers (4). The contact of the thumb (18) or grippable contact with object(s) (91) held between the thumb (18) and any one or more of the fingers (4) can be adjusted by use of a lesser or greater bend angle (87) of the intra-osseous member (11).

Figure 9:
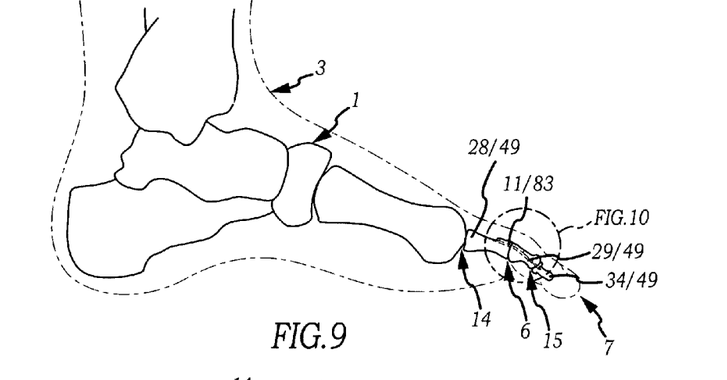
FIG. 9 is a side view of the bones of a foot which provides an example of another particular embodiment of the inventive intra-osseous member used to correct curvature of a toe.
Figure 10:
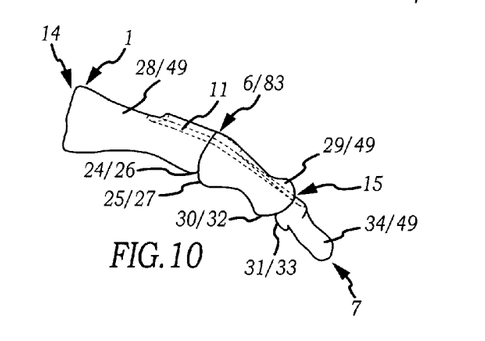
FIG. 10 is an enlargement of a part of the side view of FIG. 9 which provides a particular example of use of another particular embodiment of the inventive intra-osseous member used to correct curvature of a toe.
Figure 11:
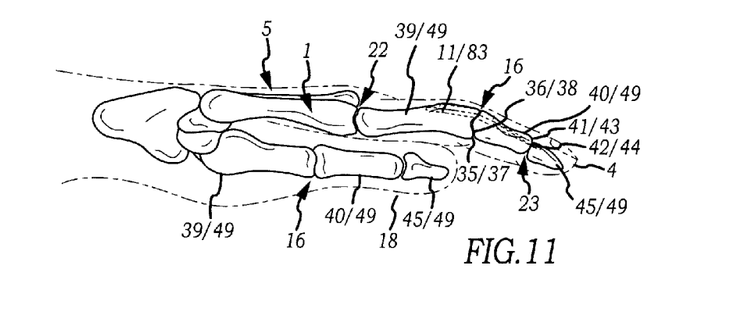
FIG. 11 is a side view of the bones of a hand which provides an example of another particular embodiment of the inventive intra-osseous member used to correct curvature of a finger.

Now referring primarily to FIGS. 9-11, which shows embodiments of the intra-osseous member (11) which further includes an elongate member (63) sufficient in length to insert a first member end (55) in the borehole (52) of a first phalanx (49) and the second member end (56) in a borehole (52) which longitudinally transverses the second phalanx (49) to establish upon forcible urging the projection element (66) in the channel (51) of the first phalanx (49) and the second phalanx (49). The second member end (56) can longitudinally traverse the second phalanx (49) in the borehole (52) which correspondingly traverses the second phalanx (49) to axially insertably engage a borehole (52) generated in a third phalanx (49). Embodiments of the intra-osseous member (11) can include a bend angle (87) which produces a desired amount of digit angle (90) in the surgically treated finger (4) or toe (2).

As can be easily understood from the foregoing, the basic concepts of the present invention may be embodied in a variety of ways. The invention involves numerous and varied embodiments of a intra-osseous fusion system which includes implantable members and methods of implanting members to allow bone on growth which achieves a level of interdigitation curvature.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implantable member" should be understood to encompass disclosure of the act of "implanting a member" —whether explicitly discussed or not—and, conversely, were there effectively disclosure of the act of "implanting a member", such a disclosure should be understood to encompass disclosure of "an implantable member" and even a "means for implanting a member." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a member" or "an elongate member" refers to one or more member(s) or at least one member. As such, the terms "a" or "an", "one or more" and "at least one" can be used interchangeably herein.

Thus, the applicant(s) should be understood to claim at least: i) an intra-osseous member as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of fusing an interphalangeal joint, comprising the step of implanting an intraosseous implant, said intraosseous implant comprising:
   a) a first end portion adapted to locate at an intraosseous position within a first phalanx;
      ii) a second end portion adapted to locate at an intraosseous position within a second phalanx;
      iii) a curved portion disposed between said first end portion and said second end portion, said curved portion adapted to traverse a distance of said interphalangeal joint to fix said first phalanx at an angle in relation to said second phalanx; and
   b) a projection element coupled lengthwise to said elongate member, said projection element adapted to locate a first part at an intraosseous position within said first phalanx and locate a second part at an intraosseous position within said second phalanx, said projection element outwardly extending from said elongate member having said intraosseous position within said first phalanx and said second phalanx a distance toward said the external surface of said first phalanx and said second phalanx sufficient to rotationally fix said first phalanx and said second phalanx in relation to said elongate member.

2. The method of fusing an interphalangeal joint of claim 1, where in said step of implanting said intraosseous implant further includes the steps of:
   a) locating a first end portion of an elongate body at an intraosseous position within a first phalanx;
   b) locating a second end portion of said elongate body at an intraosseous position within a second phalanx;
   c) traversing a distance of said interphalangeal joint with a curved portion of said elongate body, said curved portion of said elongate body disposed between said first end portion located at said intraosseous position within said first phalanx and said second end portion located at said intraosseous position within said second phalanx, thereby fixing said first phalanx at an angle in relation to said second phalanx; and
   d) locating a first part of a projection element at an intraosseous position within said first phalanx;
   e) locating a second part of said projection element at intraosseous position within said second phalanx, said projection element outwardly extending from said elongate member having said intraosseous position within said first phalanx and said second phalanx a sufficient distance toward said an external surface of said first phalanx and said second phalanx to rotationally fix said first phalanx and said second phalanx in relation to said elongate member.

3. The method of fusing an interphalangeal joint of claim 2, further comprising the steps of:
   a) generating a channel in said first phalanx, said channel having an open end which communicates with an external surface of said first phalanx and a closed end having a location at a depth within said first phalanx, said channel substantially aligned with the longitudinal midline of said first phalanx terminating at a head of said first phalanx;
   b) generating a borehole in said first phalanx which extends a distance longitudinally inward from said head of said first phalanx, said borehole located at a position within said first phalanx which adjoins a periphery of said borehole with said closed end of said channel.
   c) aligning said first part of said projection element with said channel in said first phalanx; and
   d) forcibly urging said first end portion of said elongate body into said borehole in said first phalanx to locate at said intraosseous position having said projection element located within said channel.

4. The method of fusing an interphalangeal joint of claim 3, further comprising the steps of:
   a) generating a channel in said second phalanx, said channel having an open end which communicates with an external surface of said second phalanx and a closed end having a location at a depth within said second phalanx, said channel substantially aligned with the longitudinal midline of said second phalanx terminating at a head of said second phalanx;
   b) generating a borehole within said second phalanx which extends a distance longitudinally inward from said head of said second phalanx, said borehole located at a position within said second phalanx which adjoins a periphery of said borehole with said closed end of said channel;
   c) aligning said second part of said projection element with said channel in said second phalanx; and
   d) forcibly urging said second end portion of said elongate body to locate at said intraosseous position within a first phalanx with said projection element located within said channel;
   e) traversing said distance of said interphalangeal joint with said curved portion of said elongate member.

5. The method of fusing an interphalangeal joint of claim 4, further comprising the steps of:
   a) osseointegrating said a first end portion at said intraosseous position within a first phalanx; and
   b) osseointegrating said second end portion at said intraosseous position within a second phalanx.

* * * * *